United States Patent [19]

Combs et al.

[11] Patent Number: 4,745,118

[45] Date of Patent: May 17, 1988

[54] SUBSTITUTED QUINAZOLINE-3-OXIDES PROVIDING PHARMACOLOGICAL ACTIVITY

[75] Inventors: Donald W. Combs, Piscataway; Robert Falotico, Belle Mead, both of N.J.

[73] Assignee: Ortho Pharmaceutical Corporation, Raritan, N.J.

[21] Appl. No.: 871,031

[22] Filed: Jun. 5, 1986

[51] Int. Cl.[4] .................... A61K 31/00; C07D 413/00
[52] U.S. Cl. ................................ 514/259; 514/232.8; 514/234.8; 514/267; 544/116; 544/250; 544/283
[58] Field of Search ...................... 544/283, 116, 250; 514/259, 227, 240

[56] References Cited

PUBLICATIONS

Brown, *Heterocyclic Compounds, Fused Pyrimidines*, Part 1, 1967, John Wiley & Sons, N.Y., pp. 450–452.
Fey, et al., "Chemical Abstracts", vol. 67(18), 1967, Col. 86253c.
T. Higashino, *Chem. Pharm. Bull.* Japan (1961) 9, 635.
Zenno, et al., *Chemical Abstracts*, vol. 70, (1969), Col. 28944c.
Zenno, et al., *Chemical Abstracts*, vol. 72, (1970), Col. 90506h.

*Primary Examiner*—Glennon H. Hollrah
*Assistant Examiner*—James H. Turnipseed
*Attorney, Agent, or Firm*—Benjamin F. Lambert

[57] ABSTRACT

Novel substituted quinazoline-3-oxides are disclosed as are methods of increasing cardiotonic activity and bronchodilation in which an unit dose of a composition containing an effective amount of a cardiotonic agent or a bronchodilating agent dispersed in a pharmaceutically acceptable carrier are administered to a mammalian host.

17 Claims, No Drawings

SUBSTITUTED QUINAZOLINE-3-OXIDES PROVIDING PHARMACOLOGICAL ACTIVITY

DESCRIPTION

1. Technical Field

This invention relates to pharmacologically active substituted quinazoline-3-oxides and, more particularly to new and known substituted quinazoline-3-oxides useful in producing cardiotonic activity and/or bronchodilation.

2. Background Art

Quinazoline-3-oxides are broadly known as sedatives having muscle relaxant and anticonvulsive action. Fujisawa Japanese patent publication No. 68 07952 published Mar. 26, 1968 (*Chemical Abstracts* 70: 28944c) and No. 68 07953 published on the same date teach that acetophenone oximes such as 2-aminoacetophenone oxime are reacted with triethylorthoformate to produce substituted quinazoline-3-oxides.

T. Higashino *Chem. Pharm. Bull Japan* (1961) 9 635 reported the syntheses of substituted quinazoline-3-oxides. Fujisawa Japanese patent publication No. 70 00499 (*Chemical Abstracts* 72: 90506h) discloses the syntheses of 4-methyl-6,7-dimethoxy-quinazoline-3-oxides having 2-phenyl and 2-styryl substituents. Those compounds are reported to be long lasting analgesics.

None of the above disclosures suggests that the quinazoline-3-oxides could show cardiotonic activity.

BRIEF SUMMARY OF THE INVENTION

The present invention relates to a method of producing cardiotonic and bronchodilating activity in a mammalian host by administering to that host a unit dose of a composition containing an effective amount of a substituted quinazoline-3-oxide as the active agent dispersed in a pharmaceutically acceptable carrier. The active quinazoline-3-oxides of the present invention have a structure that corresponds to the formula:

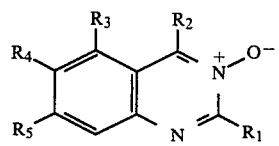

wherein:

$R_1$ is hydrogen or preferably a straight or branched alkyl radical having 1 to about 6 carbon atoms (lower alkyl), or a cycloalkyl radical having 3 to about 6 carbon atoms in the ring;

$R_2$ is hydrogen, a straight or branched lower alkyl radical having 1–6 carbon atoms or a cycloalkyl radical having 3 to about 6 carbon atoms in the ring; and $R_3$, $R_4$ and $R_5$ are the same or different radicals selected from the group consisting of hydrogen, halogen, hydroxy, lower alkyl, lower alkoxy, methylthio, methyl sulfinyl, methyl sulfonyl, lower acylamino, $NR_6R_7$ where $R_6$ and $R_7$ are the same or different and are hydrogen, a lower alkyl radical, or $NR_6R_7$ taken together form a heterocyclic ring containing 5 or 6 atoms, or where $R_4$ and $R_5$ together are methylenedioxy.

The present invention provides several benefits and advantages.

One benefit is that cardiotonic activity has been found for the novel compounds of this invention.

Another benefit is that cardiotonic activity has now been found for compounds that had hiterto not been disclosed to have such activity.

One advantage of the instant invention is that the most preferred cardiotonic agents provide an unexpectedly high degree of such activity as compared to other compounds having relatively similar substitutions.

Yet another advantage of the present invention is that certain compounds useful for producing cardiotonic activity can also produce bronchodilation so that a single agent can be administered to achieve two effects.

Still further benefits and advantages will be apparent to those skilled in the art from the detailed description that follows.

DETAILED DESCRIPTION OF THE INVENTION

The present invention contemplates a method of producing cardiotonic activity and bronchodilation, as well as the novel quinazoline-3-oxides that provide that activity.

The method of producing cardiotonic or bronchodilating activity comprises administering to a mammalian host a unit dose of a composition containing an effective amount of a cardiotonic or bronchodilating agent dispersed in a pharmaceutically acceptable carrier. The agent that is active in providing these activities is a quinazoline-3-oxide whose structure conforms to the formula:

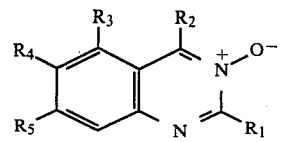

wherein $R_1$, $R_2$, $R_3$, $R_4$ and $R_5$ are as defined above.

The compounds of the present invention can be prepared according to the following reaction scheme:

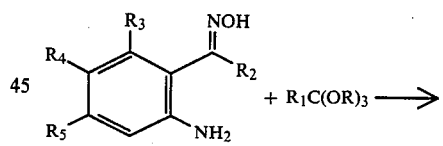

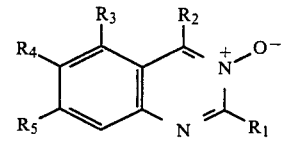

wherein $R_1$, $R_2$, $R_3$, $R_4$ and $R_5$ are as defined above and R is lower alkyl having 1 to 5 carbon atoms.

As can be seen from the above scheme an appropriately substituted acetophenone oxime is reacted with an ester of an ortho acid to form the substituted quinazoline-3-oxide. The reaction is preferably carried out at a temperaure between about 50° C. and 100° C. and is generally carried out in the absence of a solvent where one of the reactants is a liquid. The quinazoline-3-oxide product generally crystallizes in the reaction mixture and is purified by techniques known to those skilled in the art.

The preferred quinazoline-3-oxide compounds having cardiotonic and or bronchodilating activity are those in which $R_1$ is $C_1-C_3$ alkyl, $R_2$ is methyl, $R_3$ is hydrogen and $R_4$ and $R_5$ are hydrogen or $C_1-C_4$ alkoxy, especially methoxy. These $R_4$ and $R_5$ dialkoxy (dimethoxy) derivatives of the quinazoline-3-oxides disclosed herein are especially effective in producing cardiotonic activity at low dosage levels.

In examining the above structural formula to which the useful quinazoline-3-oxide compounds conform, it is noted that the $R_1$, $R_2$, $R_3$, $R_4$ and $R_5$ radicals or groups can be a "lower" alkyl, "lower" alkoxy and the like. Groups and radicals referred to as "lower" denote that they possess 1 to about 6 carbon atoms.

Straight and branched lower alkyl radicals include, for example, methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, and the like.

Lower alkoxy radicals are oxygen ethers formed from a before-described straight or branched lower alkyl group. Exemplary straight and branched lower alkoxy radicals include methoxy, ethoxy, propoxy, isopropoxy, n-butoxy, and the like.

Cycloalkyl radicals useful herein contain 3 to about 6 carbon atoms in the ring. Exemplary radicals include cyclopropyl, cyclobutyl, cyclopentyl and cyclohexyl.

Halogen radicals preferably include chloro and bromo, as well as fluoro and iodo.

$R_3$, $R_4$ or $R_5$ can be an amino radical designated $NR_6R_7$ where $R_6$ and $R_7$ are the same or different and are selected from the group consisting of hydrogen, lower alkyl radicals as described before, and $NR_6R_7$ taken together can form a heterocyclic ring containing 5 or 6 atoms. Exemplary $NR_6R_7$ radicals include amino, methylamino, isopropylamino, hexylamino, dimethylamino, diethylamino, methylbutylamino, dihexylamino, butylhexylamino, N-morpholinyl, N-pyrrolidinyl, N-piperidyl, 4-methyl-N-piperazinyl and the like.

A lower acyl amino (lower acylamido) radical is an amide that can be viewed as being formed from an $R_3$, $R_4$ or $R_5$ amino group and a straight or branched lower alkyl carboxylic acid. Exemplary of such radicals are formamido, acetamido, valerylamido, isobutyrlamido and the like.

As already noted, especially preferred cardiotonic and/or bronchodilating agents of the before-mentioned formula contain an $R_1$ group that contains 1–3 carbon atoms, an $R_2$ methyl group and $R_4$ and $R_5$ groups that are hydrogen or methoxy. In most preferred such agents, $R_3$ is hydrogen.

Those especially and most preferred cardiotonic agents include:
2,4-dimethyl-6,7-dimethoxyquinazoline-3-oxide;
2-ethyl-4-methyl-6,7-dimethoxyquinazoline-3-oxide;
2-isopropyl-4-methyl-6,7-dimethoxyquinazoline-3-oxide; and
4-methyl-6,7-dimethoxyquinazoline-3-oxide.

Those especially preferred bronchodilating agents include:
2-ethyl-4-methyl-6,7-dimethoxyquinazoline-3-oxide;
2-isopropyl-4-methyl-6,7-dimethoxyquinazoline-3-oxide;
2-n-propyl-4-methyl-6,7-dimethoxyquinazoline-3-oxide;
2-isobutyl-4-methyl-6,7-dimethoxyquinazoline-3-oxide;
2-cyclopropyl-4-methyl-6,7-dimethoxyquinaozline-3-oxide; and
2-isopropyl-4-methyl-6-amino-quinazoline-3-oxide.

It is thus seen that some of the substituted quinazoline-3-oxides are particularly effective in enhancing both cardiotonic activity and bronchodilation.

A quinazoline-3-oxide useful herein can be present in an effective amount in a cardiotonic composition or in a bronchodilating composition, and is dispersed in a pharmaceutically acceptable carrier in those compositions. Such compositions are administered in a unit dose to a mammalian host.

The term "unit dosage" and its grammatical equivalents is used herein to refer to physically discrete units suitable as unitary dosages for human patients and other mammalian host animals, each unit containing a predetermined, effective amount of the active ingredient quinazoline-3-oxide calculated to produce the desired cardiotonic activity or bronchodilating effects in association with the required pharmaceutically acceptable carrier, e.g., a diluent or a vehicle. The specifications for the novel unit dosage forms of this invention are dictated by and are directly dependent on (a) the unique characteristics of the active ingredient, and (b) the limitations inherent in the art of compounding such an active ingredient for therapeutic use in humans and other animals. Examples of suitable unit dosage forms in accord with this invention are tablets, capsules, pills, powder packets, granules, wafers, and the like, segregated multiples of any of the foregoing, as well as liquid solutions and suspensions.

The active ingredient is referred to herein as being dispersed in the carrier. The dispersion formed can be a simple admixture, a non-settling dispersion as in the case of certain emulsions, or as an ultimate dispersion, a true solution.

The amount of active ingredient that is administered in vivo depends on the age and weight of the mammal treated, the particular condition to be treated, the frequency of administration, and the route of administration. For cardiotonic activity, the dose range can be about 0.5 to about 1000 milligrams per kilogram of body weight, more preferably about 0.1 to about 500 milligrams per kilogram of body weight and most preferably about 1.0 to about 100 milligrams per kilogram of body weight. The human adult dose is in the range of about 1 to about 20 milligrams daily, given as a single dose or in 3 or 4 divided doses. Veterinary dosages correspond to human dosages with the amounts administered being in proportion to the weight of the animal as compared to adult humans.

For bronchodilation, the dose range can be about 0.1 to about 1000 milligrams per kilogram of body weight, more preferably about 1.0 to about 100 milligrams per kilogram of body weight and most preferably about 1.0 to about 50 milligrams per kilogram of body weight. The human adult dose is in the range of about 70 to about 3500 milligrams daily, given as a single dose or in 3 or 4 divided doses. Veterinary dosages correspond to human dosages with the amounts administered being in proportion to the weight of the animal as compared to adult humans.

As is seen from the data discussed hereinafter, orally administered unit doses containing about 1 to about 10 milligrams of a substituted quinazoline-3-oxide per kilogram of mongrel dog body weight were useful in producing a cardiotonic effect. The bronchodilating effects reported in Table 2 were obtained using a unit dose containing 50 milligrams per kilogram of Hartley guinea pig body weight.

Pharmaceutically acceptable carriers are well known in the art. Exemplary of liquid carriers are aqueous solutions that contain no materials in addition to the substituted quinazoline-3-oxide, or contain a buffer such as sodium phosphate at physiological pH value, normal saline, Ringer's Injection, Dextrose Injection, Dextrose and Sodium Chloride Injection, Lactated Ringer's Injection and the like.

Liquid compositions can also contain liquid phases in addition to and to the exclusion of water. Exemplary of such additional liquid phases are glycerin and vegetable oils such as corn oil and cottonseed oil.

Exemplary solid carriers (diluents) include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Antioxidants such as tocopherol, methylparaben and propylparaben can be present in both solid and liquid compositions, as can sweeteners such a cane or beet sugar, sodium saccharin, sodium cyclamate and the dipeptide methyl ester sweetener sold under the trademark NUTRASWEET (aspartame) by G. D. Searle Co.

The method comprises administering to a mammal a unit dose of a pharmaceutical composition that includes an effective amount of an active ingredient that is the before-described substituted quinazoline-3-oxide compound dispersed in a pharmaceutically acceptable carrier. The pharmaceutical composition is preferably maintained within the mammal until the compound is cleared from the mammal's body by natural means such as excretion or metabolism.

The pharmaceutical composition can be administered by any conventional route including oral, intravenous, intraperitoneal administration and by injection by means well known in the art. In preferred practice, the composition is administered orally as a tablet, capsule or aqueous dispersion.

Inasmuch as a pharmaceutical composition can be administered several times daily (per 24 hour period), the method of producing cardiotonic activity or bronchodilation can include administering the pharmaceutical composition a plurality of times into the treated mammal over a time period of weeks, months and years.

The invention is illustrated in the synthesis and assay Examples that follow.

BEST MODE FOR CARRYING OUT THE INVENTION

EXAMPLE 1

2-Ethyl-4-methylquinazoline-3-oxide

O-Aminoacetophenone oxime [5.0 grams (g), 33.3 millimoles (mmoles)] was refluxed for 1.5 hours in 45 milliliters (ml) of triethylorthopropionate. The mixture was cooled giving crystals that were collected by filtration, washed with ethanol, and then ether. 2.88 grams of product were obtained having a melting point of 146°–147° C. The mother liquor afforded four subsequent crops totalling 5.5 g (88%).

Calc. for $C_{11}H_{12}N_2O$: C, 70.16; H, 6.44; N, 14.88. Found: C, 70.06; H, 6.67; N, 14.68.

EXAMPLE 2

6-Chloro-4-methylquinazoline-3-oxide

5-Chloro-2-aminoacetophenone oxime [750 milligrams (mg), 4 mmoles] was heated at reflux in 10 ml of triethylorthoformate for 1 hour. The mixture was cooled and filtered yielding 750 mg (95%) of the desired compound having a melting point of 234°–235° C. (the melting point in the literature is 229°–230° C.)

Calc. for $C_9H_7ClN_2O$: C, 55.52; H, 3.60; N, 14.40. Found: C, 55.16; H, 3.64; N, 14.27.

EXAMPLE 3

2-Ethyl-4-methyl-6-chloroquinazoline-3-oxide

This compound was synthesized by the method of Example 1 using 2-amino-5-chloroacetophenone oxime. The yield was 46% and the product had a melting point of 140°–141° C.

Calc. for $C_{11}H_{11}ClN_2O$: C, 59.32; H, 5.00; N, 12.58. Found: C, 58.99; H, 5.03; N, 12.47.

EXAMPLE 4

4-Methyl-5,6-dimethoxyquinazoline-3-oxide

This compound was synthesized by the method of Example 2 using 2-amino-5,6-dimethoxyacetophenone oxime. The yield was 53% and the product had a melting point of 141°–143° C.

Calc. for $C_{11}H_{12}N_2O_3$: C, 60.00; H, 5.45; N, 12.73. Found: C, 59.64; H, 5.58; N, 12.42.

EXAMPLE 5

2,4-Dimethyl-5,6-dimethoxyquinazoline-3-oxide

This compound was synthesized by the method of Example 1 using triethylorthoacetate and 2-amino-5,6-dimethoxyacetophenone oxime. The yield was 50% and the product had a melting point of 122.5°–123.5° C.

Calc. for $C_{12}H_{14}N_2O_3$: C, 61.52; H, 6.04; N, 11.96. Found: C, 61.48; H, 6.18; N, 11.75.

EXAMPLE 6

2-Ethyl-4-methyl-6-methylthioquinazoline-3-oxide

This compound was synthesized by the method of Example 1 using 2-amino-5-methylthioacetophenone oxime and triethylorthoformate. The yield was 50% and the product had a melting point of 115°–117° C.

Calc. for $C_{12}H_{12}N_2O_5$: C, 61.50; H, 6.03; N, 11.96. Found: C, 61.51; H, 6.12; N, 11.68.

EXAMPLE 7

2-Ethyl-4-methyl-6-(4-methylpiperazino)quinazoline-3-oxide

This compound was synthesized by the method of Example 1 using 5-(4-methylpiperazino)-2-aminoacetophenone oxime HCl and triethylorthoformate. The yield was 62% and the melting point was 125°–127° C.

Calc. for $C_{16}H_{22}N_4O$: C, 67.09; H, 7.76; N, 19.55. Found: C, 66.78; H, 7.48; N, 19.37.

EXAMPLE 8

4-Methyl-6,7-dimethoxyquinazoline-3-oxide

This compound was synthesized by the method of Example 2 using 2-amino-4,5-dimethoxyacetophenone oxime and triethylorthoformate. The yield was 90% and the melting point was 229°–230° C.

Calc. for $C_{11}H_{12}N_2O_3$: C, 60.00; H, 5.45; N, 12.73. Found: C, 59.65; H, 5.56; N, 12.61.

EXAMPLE 9

2,4-Dimethyl-6,7-dimethoxyquinazoline-3-oxide

2-Amino-4,5-dimethoxy acetophenone oxime (3 g, 14.30 mmoles) was heated to reflux in 50 ml of triethylorthoacetate. After 2 hours, the mixture was cooled and filtered. The filtercake was washed with ethanol and dried under vacuum to give 2.1 g (63%) of the product having a melting point of 185°–186° C.

Calc. for $C_{12}H_{14}N_2O_3$: C, 61.46; H, 5.98: N, 11.95. Found: C, 61.00; H, 5.98; N, 11.96.

EXAMPLE 10

2-Ethyl-4-methyl-6,7-dimethoxyquinazoline-3-oxide

This compound was synthesized by the method of Example 9 using triethylorthopropionate instead of triethylorthoacetate. The yield was 84% and the melting point was 196°–198° C.

Calc. for $C_{13}H_{16}N_2O_3$: C, 62,88; H, 6.51; N, 11.28. Found: C, 62.69; H, 6.47; N, 11.32.

EXAMPLE 11

2-Isopropyl-4-methyl-6,7-dimethoxyquinazoline-3-oxide

2-Isobutyrylamino-4,5-dimethoxyacetophenone (5 g, 18.8 mmoles) was dissolved in 150 ml of ethanol, 18 ml of pyridine and 20 g of hydroxylamine hychrochloride, and the resulting solution refluxed overnight. The solvent was removed in vacuo, and the solid was recrystallized from methanol-water to give 4.55 g of product having a melting point of 177°–179° C.

Calc. for $C_{14}H_{18}N_2O_3$: C, 64.09, H, 6.93; N, 10.68. Found: C, 63.63, H, 7.29; N, 10.92.

EXAMPLE 12

2-Cyclopentyl-4-methyl-6,7-dimethoxyquinazoline-3-oxide

This compound was synthesized by the method of Example 11 using 2-cyclopentanecarbonylamino-4,5-dimethoxyacetophenone. The yield was 90%, and the product had a melting point of 148°–150° C.

Mass spectrum=288M+

Calc. for $C_{16}H_{20}N_2O_3(H_2O)$: C, 62.72; H, 7.25; N, 9.14. Found: C, 63.00; H, 6.90; N, 9.14.

EXAMPLE 13

2-nPropyl-4-methyl-6,7-dimethoxyquinazoline-3-oxide

This compound was synthesized by the method of Example 11 using 2-n-butyrylamino-4,5-dimethoxyacetophenone. The yield was 93% and the product had a melting point of 139°–141° C.

Calc. for $C_{15}H_{18}N_2O_3$: C, 64.09; H, 6.93; N, 10.68. Found: C, 64.03; H, 6.90; N, 10.95.

EXAMPLE 14

2-Cyclobutyl-4-methyl-6,7-dimethoxyquinazoline-3-oxide

This compound was synthesized by the method of Example 11 using 2-cyclobutanecarbonylamino-4,5-dimethoxy-acetophenone. The product was obtained in a yield of 89% yield and had a melting point of 160°–163° C.

Calc. for $C_{15}H_{18}N_2O_3$: C, 65.66; H, 6.63; N, 10.21. Found: C, 65.63; H, 6.63; N, 10.01.

EXAMPLE 15

2-Isobutyl-4-methyl-6,7-dimethoxyquinazoline-3-oxide

This compound was synthesized by the method of Example 11 using 2-isovalerylamino-4,5-dimethoxyacetophenone. The product was obtained in a yield of 86% and had a melting point of 130°–132° C.

Calc. for $C_{15}H_2ON_2O_3(\frac{1}{2}H_2O)$: C, 65.17; H, 7.31; N, 10.14. Found: C, 65.38; H, 7.44; N, 10.27.

EXAMPLE 16

2-Isopropyl-4-methylquinazoline-3-oxide 7.6 Grams of 2-aminoacetophenone oxime were dissolved in 75 ml of acetic acid and 5.5 ml of isobutyryl chloride (1.1 equivalents) were added. The mixture was heated to a temperature of 60°–70° C. for a period of 3 hours, giving a clear solution. The acetic acid so formed was removed at reduced pressure and the residue was crystallized from ethanol to give 1.28 g of product. The mother liquor was further chromatographed on silica gel and eluted with methylene chloride-methanol 95:5 to give about 1.0 g of product having a melting point of 115°–117° C.

Calc. for $C_{12}H_{14}N_2O$: C, 71.24; H, 6.99; N, 13.85. Found: C, 71.19; H, 7.16; N, 13.65.

EXAMPLE 17

2-Isopropyl-4-methyl-6-butylquinazoline-3-oxide

This compound was synthesized by the method of Example 11 using 2-isobutyrylamino-5-butylacetophenone. The product was obtained in a yield of 89% and melted at 67.5°–68.5° C.

Calc. for $C_{16}H_{22}N_2O$: C, 74.38; H, 8.58; N. 10.84. Found: C, 74.44; H, 8.79; N, 10.93.

EXAMPLE 18

2-Cyclopropyl-4-methyl-6,7-dimethoxyquinazoline-3-oxide

This compound was synthesized by the method of Example 11 using 2-cyclopropylcarbonylamino-4,5-dimethoxyacetophenone. The product was obtained in a yield of 62% yield and had a melting point of 182°–184° C.

Calc. for $C_{14}H_{16}N_2O_3$: C, 64.59; H, 6.21; N, 10.76. Found: C, 64.47; H, 6.26; N, 10.75.

EXAMPLE 19

2-Ethyl-6,7-methylenedioxyquinazoline-3-oxide

This compound was synthesized by the method of Example 1 using 2-aminopiperonal oxime. The product was obtained in a yield of 84% and had a melting point of 217°–218° C.

Calc. for $C_{11}H_{10}N_2O_3$: C, 60.55; H, 4.59; N, 12.84. Found: C, 60.38; H, 4.71; N, 12.86.

EXAMPLE 20

2-nButyl-4-methyl-6,7-dimethoxyquinazoline-3-oxide

This compound was synthesized by the method of Example 1 using 2-amino-4,5-dimethoxyacetophenone oxime and trimethylorthovalerate. The product was obtained in a yield of 90% and had a melting point of 138°–141° C.

Calc. for $C_{15}H_{20}N_2O_3$: C, 65.18; H, 7.31; N, 10.14. Found: C, 65.13; H, 7.53; N, 9.94.

EXAMPLE 21

2-nPentyl-4-methyl-6,7-dimethoxyquinazoline-3-oxide

This compound was synthesized by the method of Example 11 using 2-n-hexanoylamino-4,5-dimethoxyacetophenone. The product was obtained in a yield of 81% and had a melting point of 159°–162° C.

Calc. for $C_{16}H_{22}N_2O_3$: C, 66.17; H, 7.65; N, 9.65. found: C, 66.36; H, 7.88; N, 9.72.

EXAMPLE 22

2-Isopropyl-4-methyl-6-fluoroquinazoline-3-oxide

This compound was synthesized by the method of Example 11 using 2-isobutyrylamino-5-fluoroacetophenone as the precursor. The product was obtained in a yield of 40%, and had a melting point of 142°–144° C.

Calc. for $C_{12}H_{13}FN_2O$: C, 65.42; H, 5.96; N, 12.72. Found: C, 65.29; H, 5.93; N, 12.77.

EXAMPLE 23

6-Amino-2-isopropyl-4-methylquinazoline-3-oxide

This compound was synthesized by the method of Example 11 using 2-isobutrylamino-5-amino-acetophenone as the precursor. The product was obtained in a yield of 12% and had a melting point of 185°–186.5° C.

Calc. for $C_{12}H_{15}N_3O$: C, 66.32; H, 6.97; N, 19.34. Found: C, 66.07; H, 7.00; N, 18.98.

EXAMPLE 24

6-Methylthio-2-isopropyl-4-methylquinazoline-3-oxide

This compound was synthesized by the method of Example 11 using 2-isobutyrylamino-5-methylthioacetophenone. The product was obtained in a yield of 31% and had a melting point of 105°–108° C.

Calc for $C_{13}H_{16}N_2OS$: C, 62.87; H, 6.49; N, 11.28. Found: C, 62.76; H, 6.48; N, 11.16.

EXAMPLE 25

6-Dimethylamino-2-isopropyl-4-methylquinazoline-3-oxide

This compound was synthesized by the method of Example 11 using 2-isobutyrylamino-5-dimethylamino acetophenone. The product was obtained in a yield of 28% and melted at 136°–137° C.

Calc for $C_{14}H_{19}N_3O$: C, 68.53; H, 7.82; N, 17.13. Found: C, 68.58; H, 7.83; N, 17.10.

EXAMPLE 26

Cardiotonic Activity

Cardiotonic activity is defined as an increase in myocardial contractile performance as determined by measurements made using a Walton-Brodie strain gauge. The procedure for measuring cardiotonic activity is standard, and is reported in Alousi, et al., "Cardiotonic Activity of Amrinone—Win 40680", Circ. Res. 45: 666 (1979).

In the procedure utilized, adult mongrel dogs are anesthetized with sodium pentobarbital and are artifically respired. Arterial pressure is recorded via a femoral artery and the pressure pulse is used to trigger a cardiotachometer for heart rate. Left ventricular pressure is measured with a Millar catheter and change of pressure with change of time (dP/dt) is derived. Cardiac output is determined by measuring ascending aortic blood flow with an electromagnetic flow probe, and myocardial contractile force is measured with a Walton-Brodie strain gauge sutured to the right ventricle. Lead II electrocardiogram (EKG) is also recorded.

A standard dose of dopamine or dobutamine is administered to assess myocardial responsiveness.

Assayed compounds are administered by intravenous infusion or bolus administration and the efects on cardiovascular parameters are determined.

The dosage of drug is reported in milligrams per kilogram of the mammalian host treated.

The cardiotonic activity is then reported as the percentage increase or decrease in the strain gauge reading.

The compounds of this invention were assayed for their cardiotonic activity using the assay procedure above described. The results of those assays are illustrated in Table 1, below, wherein $R_1$, $R_2$, $R_3$, $R_4$ and $R_5$ of the structural formula are as shown in the Table.

TABLE 1

| | | | Cardiotonic Activity | | | |
|---|---|---|---|---|---|---|
| Ex.[a] | $R_5$ | $R_4$ | $R_3$ | $R_2$ | $R_1$ | C.A.[b] |
| 1 | H | H | H | Me | Et | 47 |
| 2 | H | Cl | H | Me | H | 51[c] |
| 3 | H | Cl | H | Me | Et | 53 |
| 4 | H | OMe | OMe | Me | H | 48[c] |
| 5 | H | OMe | OMe | Me | Me | 43[c] |
| 6 | H | SCH$_3$ | H | Me | Et | 70 |
| 8 | OMe | OMe | H | Me | H | 54[c] |
| 9 | OMe | OMe | H | Me | Me | 124[c] |
| 10 | OMe | OMe | H | Me | Et | 229[c] |
| 11 | OMe | OMe | H | Me | iPr | 150 |
| 20 | OMe | OMe | H | Me | nBu | 25 |

Note [a]Compounds of Examples as numbered.
Note [b]Cardiotonic Activity (C.A.) assayed by the increase in cardiac force in percent as measured by Walton-Brodie strain gauge in the previously described procedure using a dosage of 1.87 milligrams per kilogram of anesthetized dog's body weight.
Note [c]Same as Note b, but at 8.75 milligrams per kilogram.

In the above Table, "H" is hydrogen, "Me" is methyl, "Et" is ethyl, "iPr" is isopropyl, "nBu" is normal-butyl, "OMe" is methoxy, "Cl" is chloro and "SCH$_3$" is thiomethyl.

EXAMPLE 27

Bronchodilation

Bronchodilation can be equated to the inhibition of bronchoconstriction. Bronchoconstriction induced by ovalbumin injection (anaphylaxis) is measured as a percent of maximum bronchoconstriction obtained by clamping off the trachea as control. Percent inhibition of control is determined using the equation:

$$\% \text{ Inhibition of Control} = \frac{(\text{Control } \% \text{ Max.BC}) - (\text{Treated } \% \text{ Max.BC}) \times 100}{\text{Control } \% \text{ Max.BC}}$$

wherein "Max.BC" is maximum bronchoconstriction.

This procedure for measuring bronchodilation is also a standard method and is substantially that reported by Ritchie et al., "SRS-A Medicated Bronchospasm by Pharmacologic Modification of Lung Anaphylaxis In Vivo," Agents and Actions, 11: 4 (1981).

In accordance with that procedure, male Hartley guinea pigs are actively sensitized intraperitoneally with 16 milligrams (mg) alum and 1 mg ovalbumin. Fourteen days later, the animals are anesthetized and respiration is arrested by the administration of succinylcholine. Respiration is maintained at a constant pressure by a miniature Startling pump. Lung overflow changes in pressure are recorded.

Animals are pretreated with indomethacin [10 mg/kilogram of body weight (mg/kg), intravenously (i.v.)], atropine (0.5 mg/kg, i.v.), methylsergide (0.1 mg/kg, i.v.), methapyrilene (2.0 mg/kg, i.v.), and arachidonic acid (5.0 mg/kg, i.v.), prior to ovalbumin challenge. Bronchodilating agents in an appropriate physiologically tolerable carrier are administered by various routes prior to ovalbumin provocation. Indications of efficacy are manifested as a substantial reduction in (inhibition of) the degree of bronchoconstriction evidenced by control animals.

The percent inhibition of control is calculated by the equation above. Percentage values greater than 20 percent are considered to be manifestations of efficacy.

The substituted guinazoline-3-oxides described herein were assayed for their ability to produce bronchodilation using the before-described procedure. The results of those assays are illustrated in Table 2, below, wherein $R_1$, $R_2$, $R_3$, $R_4$, and $R_5$ of the structural formula are as shown in the Table.

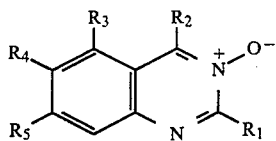

TABLE 2

| Ex.[a] | BRONCHODILATING ACTIVITY | | | | | |
|---|---|---|---|---|---|---|
| | $R_5$ | $R_4$ | $R_3$ | $R_2$ | $R_1$ | % BD-[b] |
| 1 | H | H | H | Me | Et | 43.6 |
| 9 | OMe | OMe | H | Me | Me | 45.7 |
| 10 | OMe | OMe | H | Me | Et | 85.9 |
| 11 | OMe | OMe | H | Me | iPr | 89.8 |
| 12 | OMe | OMe | H | Me | cPe | 47.8 |
| 13 | OMe | OMe | H | Me | nPr | 87.2 |
| 14 | OMe | OMe | H | Me | cBu | 37.1 |
| 15 | OMe | OMe | H | Me | iBu | 96.2 |
| 16 | H | H | H | Me | iPr | 89.0 |
| 17 | H | Bu | H | Me | iPr | 58.8[c] |
| 18 | OMe | OMe | H | Me | cPr | 93.6[c] |
| 19 | —OCH$_2$O— | | H | H | Et | 65.1 |
| 20 | OMe | OMe | H | Me | nBu | 68.5 |
| 21 | OMe | OMe | H | Me | nPe | 43.8 |
| 22 | H | F | H | Me | iPr | 55.1 |
| 23 | H | NH$_2$ | H | Me | iPr | 93.4 |
| 24 | H | SMe | H | Me | iPr | 71.2 |
| 25 | H | NMe$_2$ | H | Me | iPr | 48.7 |

Note [a]Compounds of Examples as numbered.
Note [b]Percent Bronchodilation (% BD) assayed as described before using a unit dose containing 50 mg/kg of Hartley guinea Pigs.
Note [c]At a dose of 25 mpk.

Abbreviations in the above Table 2 are as in Table 1. In addition, "cPe", "cBu", "cHe" and cPr are cyclopentyl, cyclobutyl, cyclohexyl, and cyclopropyl respectively, "nPe" is normal-pentyl, "NO$_2$" in nitro, "—OCH$_2$O—" is methylenedioxy, "NH$_2$" is amino, "NHAc" is N-acetyl, and "NMe$_2$" is dimethylamino.

The present invention has been described with respect to preferred embodiments. It will be clear to those skilled in the art that modifications and/or variations of the disclosed subject matter can be made without departing from the scope of the invention set forth herein.

What is claimed is:

1. A substituted quinazoline-3-oxide having a structure conforming to the formula:

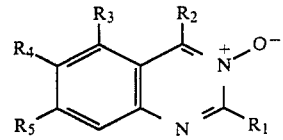

wherein
$R_1$ is a radical selected from the group consisting of straight or branched lower alkyl and cycloalkyl having 3 to about 6 carbon atoms in the ring;

$R_2$ is selected from the group of radicals consisting of hydrogen, straight or branched lower alkyl and cycloalkyl having 3 to about 6 carbon atoms in the ring;

$R_3$, $R_4$ and $R_5$ are the same or different and are selected from the group of radicals consisting of hydrogen, halogen, hydroxy, lower alkyl, lower alkoxy, methylthio, lower acylamino, NR$_6$R$_7$ where $R_6$ and $R_7$ are the same or different lower alkyl or NR$_6$R$_7$ taken together form a heterocyclic ring having 5 or 6 atoms selected from N-morpholinyl, N-pyrrolidenyl, N-piperidyl and 4-methyl-N-piperazinyl, and where $R_4$ and $R_5$ together are methylenedioxy provided that $R_3$, $R_4$ and $R_5$ are not simultaneously hydrogen.

2. A substituted quinazoline-3-oxide as recited in claim 1 in which $R_4$ and $R_5$ are the same and are both $C_1$–$C_4$ alkoxy.

3. A substituted quinazoline-3-oxide as recited in claim 2 in which $R_1$ is $C_1$–$C_3$ alkyl.

4. A substituted quinazoline-3-oxide as recited in claim 3 in which $R_3$ is hydrogen and $R_4$ and $R_5$ are methoxy.

5. A substituted quinazoline-3-oxide as recited in claim 4 in which $R_1$ is ethyl.

6. A substituted quinazoline-3-oxide as recited in claim 2 that is 2,4-dimethyl-6,7-dimethoxyquinazoline-3-oxide.

7. A substituted quinazoline-3-oxide as recited in claim 2 that is 2-ethyl-4-methyl-6,7-dimethoxyquinazoline-3-oxide.

8. A substituted quinazoline-3-oxide as recited in claim 2 that is 2-isopropyl-4-methyl-6,7-dimethoxyquinazoline-3-oxide.

9. A substituted quinazoline-3-oxide as recited in claim 2 that is 2-isobutyl-4-methyl-6,7-dimethoxyquinazoline-3-oxide.

10. A substituted quinazoline-3-oxide as recited in claim 2 that is 2-n-propyl-4-methyl-6,7-dimethoxyquinazoline-3-oxide.

11. A substituted quinazoline-3-oxide as recited in claim 1 that is 2-isopropyl-4-methylquinazoline-3-oxide.

12. A method of producing cardiotonic and/or bronchodilating activity comprising administering a unit dose of a cardiotonic composition to a mammalian host, said composition containing an effective amount of a cardiotonic or bronchodilating agent of claim 1 dispersed in a pharmaceutically acceptable carrier, said agent having a structure that corresponds to the formula

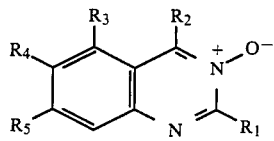

wherein
- $R_1$ is a radical selected from the group consisting of hydrogen, straight or branched lower alkyl and cycloalkyl having 3 to about 6 carbon atoms in the ring;
- $R_2$ is a radical selected from the group consisting of hydrogen, straight or branched lower alkyl and cycloalkyl having 3 to about 6 carbon atoms in the ring;
- $R_3$, $R_4$ and $R_5$ are the same or different and are selected from the group of radicals consisting of hydrogen, halogen, hydroxy, lower alkyl, lower alkoxy, methylthio, lower acylamino, $NR_6R_7$ where $R_6$ and $R_7$ are the same or different and are hydrogen, lower alkyl or $NR_6R_7$ taken together form a heterocyclic ring having 5 or 6 atoms selected from N-morpholinyl, N-pyrrolidenyl, N-piperidyl and 4-methyl-N-piperazinyl, and where $R_4$ and $R_5$ together are methylenedioxy.

13. A method as recited in claim 12 in which $R_1$ is an alkyl group.

14. A method as recited in claim 13 in which $R_4$ and $R_5$ are the same and both are $C_1$–$C_4$ alkoxy.

15. A method as recited in claim 14 in which $R_1$ is $C_1$–$C_3$ straight or branched alkyl.

16. A method as recited in claim 15 in which $R_3$ is hydrogen and $R_4$ and $R_5$ are methoxy.

17. A method as recited in claim 16 in which $R_1$ is isopropyl.

* * * * *